United States Patent [19]

Björck

[11] Patent Number: 5,164,312

[45] Date of Patent: Nov. 17, 1992

[54] METHOD FOR STABILIZING THE ENZYME LACTOPEROXIDASE IN PRODUCTS

[75] Inventor: Karl E. L. Björck, Uppsala, Sweden

[73] Assignee: Ewos Aktiebolag, Sweden

[21] Appl. No.: 517,539

[22] Filed: Apr. 26, 1990

Related U.S. Application Data

[63] Continuation of Ser. No. 67,489, Jun. 26, 1987, abandoned.

[30] Foreign Application Priority Data

Jun. 30, 1986 [SE] Sweden .............................. 86029048

[51] Int. Cl.$^5$ ........................... C12N 9/96; C12N 9/08
[52] U.S. Cl. ................................. 435/188; 435/192; 426/61; 426/588
[58] Field of Search ................. 435/192, 188; 426/61, 426/588, 580

[56] References Cited

U.S. PATENT DOCUMENTS

| | | | |
|---|---|---|---|
| 4,328,312 | 4/1982 | Tsurumi et al. | 435/192 |
| 4,376,126 | 3/1983 | Evers | 426/43 |
| 4,617,190 | 10/1986 | Montgomery | 426/61 |

FOREIGN PATENT DOCUMENTS 0179486 10/1985 European Pat. Off. .

*Primary Examiner*—Charles L. Patterson, Jr.
*Attorney, Agent, or Firm*—Brumbaugh, Graves, Donohue & Raymond

[57] ABSTRACT

The present invention relates to a method for obtaining an increased stability at storage of the enzyme lactoperoxidase in particularly dry products, as well as such products, whereby the hydrogen ion concentration is adjusted to $10^{-3.25} - 10^{-6}$.

6 Claims, No Drawings

METHOD FOR STABILIZING THE ENZYME LACTOPEROXIDASE IN PRODUCTS

This application is a continuation of application Ser. No. 07/067,489, filed on Jun. 26, 1987.

DESCRIPTION

1. Technical Field

The present invention relates to a method for stabilizing the enzyme lactoperoxidase in various products, and such products comprising lactoperoxidase.

The object of the present invention is to obtain a possibility of storing the enzyme lactoperoxidase without losses, or more correct, without substantial losses of enzyme activity.

2. Background of the Invention

It has been known for some years to use the enzyme lactoperoxidase together with a tiocyanate and a hydrogen peroxide donor to prolong the freshness of milk, and to produce antibacterial compositions active in the gastro-intestinal tract against diarrhea and other intestinal disturbances.

The enzyme lactoperoxidase used in these compositions is recovered and isolated normally from bovine milk, or, more common, dried milk products are used as a lactoperoxidase enzyme source. The enzyme is thus heat stable to such an extent that it is not deactivated at the drying process to any substantial extent. However, it has turned out that the enzyme is not stable at storage to a desired extent in the dried products/compositions.

Attempts made to stabilize the storability by adding antioxidantia have turned out to be of no effect. Hereby, one thought that lack of stability was dependent on an oxidation of the hem-group of the enzyme.

Requests for a stable, storable form of lactoperoxidase have however been made since various products, feedstuffs and foodstuffs, particularly in dry form, must possess a fair storage time. Normally, at least 3-6 months will run before the product has gone all the way from producer/production, and, via retailer been completely used by the customer/consumer. The requests for stability of pharmaceutical preparations are still much greater.

DESCRIPTION OF THE PRESENT INVENTION

It has now surprisingly been shown to be possible to obtain a storage-stable product comprising lactoperoxidase by means of the present invention, which is characterized in that a product comprising the enzyme lactoperoxidase is adjusted with regard to pH, so that the pH is 3.25-6, preferably 3.25-5, more preferably 3.5-4.5 on dissolution in water.

The term product comprising lactoperoxidase means above, primarily milk products, such a whole milk, nonfat milk, various types of whey, as well as other foodstuffs and feedstuffs, and pharmaceuticals to which the enzyme lactoperoxidase is added.

The invention will be described more in detail in the following with reference to some examples of which the stability at storage of enzyme lactoperoxidase is clearly evident.

EXAMPLE 1

Whey was produced by precipitating the casein by adding rennet to fresh milk. The fraction of whey was divided into three parts of which pH was adjusted using 1M NaOH, and 1M HCl, respectively, to pH 8, 6, and 4. The samples were freeze-dried and stored at 37° C. The LP-activity of the samples were determined after storage after varying long term storage using a standardized method. The results are given in Table 1.

| Storage time | LP-activity* mU/ml (10% solution) | | |
|---|---|---|---|
| days | pH 4 | pH 6 | pH 8 |
| 13 | 873 | — | 717 |
| 21 | 1017 | 1042 | 200 |
| 36 | (1840) | 1287 | 167 |
| 93 | 810 | 327 | 37 |
| 121 | 883 | 418 | 25 |
| 190 | 617 | 260 | 23 |
| 228 | 640 | 192 | 22 |

*LP-activity in whey prior to drying was 915 mU/ml.

EXAMPLE 2

A further test was carried out in the same way as in Example 1 above, whereby pH was adjusted to 5, 6, and 8. The results obtained are given in Table 2 below.

TABLE 2

| Storage time | LP-acitivity* in mU/ml (10% solution) | | |
|---|---|---|---|
| days | pH 5 | pH 6 | pH 8 |
| 0 | 835 | 513 | 600 |
| 23 | 755 | 417 | 517 |
| 56 | 740 | 463 | 400 |
| 94 | 623 | 317 | 225 |

*LP-activity of the whey prior to drying was 1000 mU/ml

In a further test series the same freeze-dried whey was used, whereby pH was varied from 2.5 to 4.0. The results obtained are evident from Table 3 below.

TABLE 3

| | LP-activity in mU/ml (10% solution) after | | |
|---|---|---|---|
| pH | 0 | 3 | 5 weeks |
| 2.5 | 0 | 0 | 0 |
| 2.75 | 0 | 0 | 0 |
| 3.0 | 0 | 0 | 0 |
| 3.25 | 73 | 57 | 58 |
| 3.5 | 167 | 137 | 117 |
| 3.75 | 165 | 138 | 124 |
| 4.0 | 137 | 124 | 135 |

In a further test series for a further longer period of time the tests above were confirmed. The results are given in Table 4 below.

TABLE 4

| | LP-activity in mU/ml 10% solution) after | | | | | |
|---|---|---|---|---|---|---|
| pH | 0 | 2 | 4 | 6 | 11 | 18 weeks |
| 3.0 | 0 | 0 | 0 | 0 | 0 | 0 |
| 4.0 | 177 | 154 | 166 | 144 | 134 | 153 |
| 5.0 | 190 | 177 | 164 | 138 | 123 | 101 |
| 6.0 | 219 | 185 | 145 | 121 | 123 | 112 |
| 7.0 | 231 | 154 | 139 | 121 | 111 | 87 |
| 8.0 | 208 | 149 | 120 | 96 | 96 | 96 |

In a third, further test series a spray dried whey powder without LP-activity was tested, which powder was dissolved in water, whereupon pure LP enzyme was added and pH was adjusted, the samples were freeze-dried, and then stored at 37° C. The results obtained from these tests are evident from Table 5 below.

TABLE 5

| pH | LP-activity in mU/ml (10% solution) after | | | | |
|---|---|---|---|---|---|
| | 0 | 3 | 6 | 13 | 16 weeks |
| 3.5 | 355 | 409 | 255 | 330 | 380 |
| 4.0 | 370 | 378 | 243 | 328 | 314 |
| 5.0 | 409 | 365 | 221 | 240 | 241 |
| 6.0 | 386 | 347 | 182 | 212 | 191 |
| 7.0 | 401 | 286 | 158 | 165 | 144 |
| 8.0 | 332 | 247 | 136 | 163 | 134 |
| 9.0 | 363 | 247 | 148 | 144 | 108 |

As evident from the above the analyses in Example 1 have varied to some extent, but the results still consequently show that the inactivation of lactoperoxidase takes place considerably slower at a lower pH.

It is thus evident from the above given tests that the inactivation of the enzyme lactoperoxidase takes place considerably slower in lower pH, 3.25-6 than in a higher pH. The inactivation at pH 3 is immediate.

In all products, even if they should be dried, there is some moisture present, and thus a pH is present in the micro environment. By adding an acid, or a buffering system to the already dry product in such an amount that at the dissolution of the product in water one obtains a pH of 3.25-6, it has however, turned out that the stability is radically improved. A stabilization is thus already achieved by adjusting the micro environment, therefore a dissolution with accompanying pH adjustment and final drying is not necessary to obtain an effect.

In order to adjust pH any inorganic or organic acid can be used, such as hydrochloric acid, sulphuric acid, nitric acid, citric acid, acetic acid, formic acid, and others, as well as acidifying buffering systems, as citric acid-citrate buffering systems, phosphoric acid-phosphate buffering systems, and others.

It is evident that in those cases where the product should have a pH of below 3.25 prior to addition of lactoperoxidase, an addition of an alkalizing agent of the type NaOH, or $NaHCO_3$, $Na_2CO_3$ or buffering system shall take place.

I claim:

1. A method for increasing the storage stability of a freeze-dried whey composition containing active lactoperoxidase, which comprises adding a pH adjusting agent to the product, such that the pH of the product on dissolution in water is from 3.25 to 5.

2. The method according to claim 1, wherein the pH is from 3.5 to 4.5.

3. The method according to claim 1, wherein the pH adjusting agent is selected from the group consisting of hydrochloric acid, sulphuric acid, nitric acid, citric acid, acetic acid, formic acid, a citric acid-citrate buffering system, and a phosphoric acid-phosphate buffering system.

4. A freeze-dried whey composition having increased storage stability, which comprises active lactoperoxidase, a pH adjusting agent, and a material selected from the group consisting of foodstuffs and pharmaceutical preparations, wherein the pH of the product is from 3.25 to 5 on dissolution in water.

5. The product according to claim 4, wherein the pH is from 3.5 to 4.5.

6. The product according to claim 4, wherein the pH adjusting agent is selected from the group consisting of hydrochloric acid, sulphuric acid, nitric acid, citric acid, acetic acid, formic acid, a citric acid-citrate buffering system, and a phosphoric acid-phosphate buffering system.

* * * * *